United States Patent
Veliah et al.

(10) Patent No.: US 9,361,076 B1
(45) Date of Patent: Jun. 7, 2016

(54) METHOD AND SYSTEM FOR ENABLING LEGACY PATIENTS CLINICAL DOCUMENTS FOR OPEN SHARING

(75) Inventors: Shanmugasundaram Veliah, San Jose, CA (US); Lalith G. Subramanian, San Ramon, CA (US)

(73) Assignee: EMC Corporation, Hopkinton, MA (US)

( * ) Notice: Subject to any disclaimer, the term of this patent is extended or adjusted under 35 U.S.C. 154(b) by 258 days.

(21) Appl. No.: 13/537,921

(22) Filed: Jun. 29, 2012

(51) Int. Cl.
*G06F 17/30* (2006.01)
*G06F 9/45* (2006.01)

(52) U.S. Cl.
CPC ..................................... *G06F 8/433* (2013.01)

(58) Field of Classification Search
CPC .... G06Q 50/24; G06Q 10/00; G06F 17/3089; G06F 19/322; G06F 19/3443; G06F 2216/03; G06F 7/02; G06F 2207/025; G06K 2209/01
See application file for complete search history.

(56) References Cited

U.S. PATENT DOCUMENTS

| | | | |
|---|---|---|---|
| 7,590,617 B1* | 9/2009 | Voigt et al. | 707/999.003 |
| 8,645,421 B2* | 2/2014 | Meric et al. | 707/778 |
| 2003/0009420 A1* | 1/2003 | Jones | 705/39 |
| 2008/0005138 A1* | 1/2008 | Gauthier et al. | 707/101 |
| 2013/0238621 A1* | 9/2013 | Ganjam et al. | 707/737 |

\* cited by examiner

*Primary Examiner* — Yuk Ting Choi
(74) *Attorney, Agent, or Firm* — Dergosits & Noah LLP; Todd A. Noah

(57) ABSTRACT

A healthcare information infrastructure stores and registers clinical documents. The infrastructure requires that the stored documents be registered using certain metadata. Metadata associated with legacy documents is reviewed to determine whether any required metadata is missing. Any required metadata that is missing is obtained. The metadata is augmented with the obtained metadata so that the document can be stored and registered in the healthcare information infrastructure.

20 Claims, 9 Drawing Sheets

| Required Field | Equivalent (Mapped) Field |
|---|---|
| Author | Creator |
| Hospital | Institution, Facility |
| Date of Service | Date of Exam, Date of Procedure |
| . . . | . . . |

Figure 9

METHOD AND SYSTEM FOR ENABLING LEGACY PATIENTS CLINICAL DOCUMENTS FOR OPEN SHARING

BACKGROUND

The present invention relates to the field of information technology, including, more particularly, to systems and techniques for integrating legacy clinical documents into a Cross-Enterprise Document Sharing (XDS) infrastructure.

Global healthcare organizations are increasingly being pressured to share information to improve the delivery of patient care, coordinate patient financial services, and enable the adoption of the electronic health record. An interoperable healthcare environment allows siloed patient health information to be shared securely in order to gain a holistic view of the patient, improve the quality and efficiency of care, and control health information technology ("IT") costs. Health IT interoperability is not only "a must" for collaborative healthcare, but it also greatly increases the value of technology investments made in healthcare organizations.

Clinical documents generated before the development of standards for sharing healthcare information may not be compliant with the standards. As a result, these legacy clinical documents may not be available through systems designed according to current standards.

Thus, there is a need to provide systems and techniques to make legacy clinical documents available through such systems in order to share healthcare information.

BRIEF DESCRIPTION OF THE FIGURES

FIG. 9 shows an example of a transformation table.

DETAILED DESCRIPTION

Figure 1:
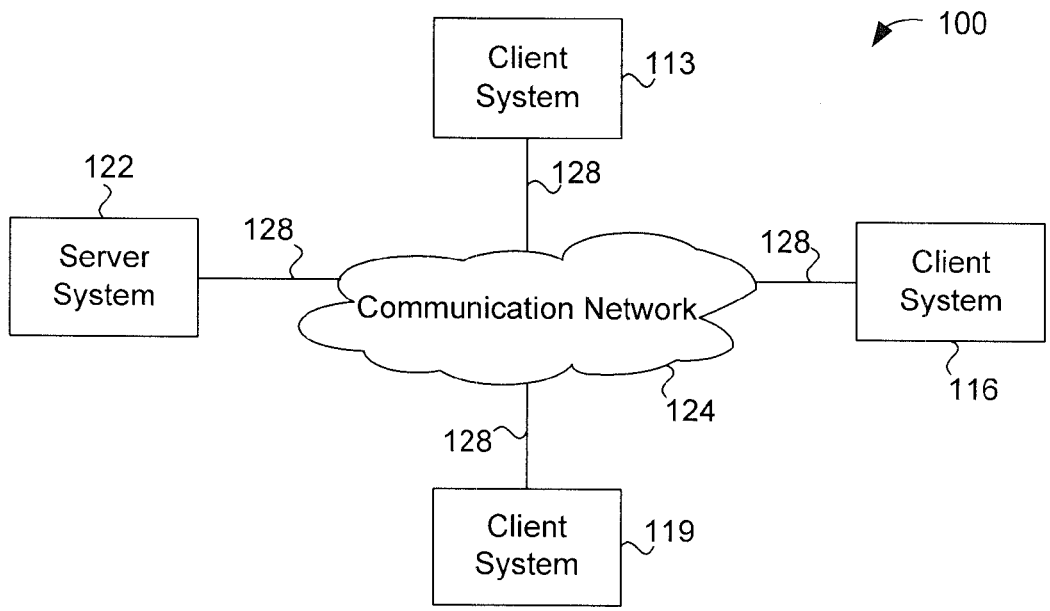
FIG. 1 shows a block diagram of a client-server system and network in which an embodiment of the invention may be implemented.

FIG. 1 is a simplified block diagram of a distributed computer network 100. Computer network 100 includes a number of client systems 113, 116, and 119, and a server system 122 coupled to a communication network 124 via a plurality of communication links 128. There may be any number of clients and servers in a system. Communication network 124 provides a mechanism for allowing the various components of distributed network 100 to communicate and exchange information with each other.

Communication network 124 may itself be comprised of many interconnected computer systems and communication links. Communication links 128 may be hardwire links, optical links, satellite or other wireless communications links, wave propagation links, or any other mechanisms for communication of information. Various communication protocols may be used to facilitate communication between the various systems shown in FIG. 1. These communication protocols may include TCP/IP, HTTP protocols, wireless application protocol (WAP), vendor-specific protocols, customized protocols, and others. While in one embodiment, communication network 124 is the Internet, in other embodiments, communication network 124 may be any suitable communication network including a local area network (LAN), a wide area network (WAN), a wireless network, a intranet, a private network, a public network, a switched network, and combinations of these, and the like.

Distributed computer network 100 in FIG. 1 is merely illustrative of an embodiment and is not intended to limit the scope of the invention as recited in the claims. One of ordinary skill in the art would recognize other variations, modifications, and alternatives. For example, more than one server system 122 may be connected to communication network 124. As another example, a number of client systems 113, 116, and 119 may be coupled to communication network 124 via an access provider (not shown) or via some other server system.

Client systems 113, 116, and 119 typically request information from a server system which provides the information. For this reason, server systems typically have more computing and storage capacity than client systems. However, a particular computer system may act as both a client or a server depending on whether the computer system is requesting or providing information. Additionally, although aspects of the invention have been described using a client-server environment, it should be apparent that the invention may also be embodied in a stand-alone computer system. Aspects of the invention may be embodied using a client-server environment or a cloud-computing environment.

Server 122 is responsible for receiving information requests from client systems 113, 116, and 119, performing processing required to satisfy the requests, and for forwarding the results corresponding to the requests back to the requesting client system. The processing required to satisfy the request may be performed by server system 122 or may alternatively be delegated to other servers connected to communication network 124.

Client systems 113, 116, and 119 enable users to access and query information stored by server system 122. In a specific embodiment, a "Web browser" application executing on a client system enables users to select, access, retrieve, or query information stored by server system 122. Examples of web browsers include the Internet Explorer® browser program provided by Microsoft® Corporation, and the Firefox® browser provided by Mozilla® Foundation, and others.

Figure 2:
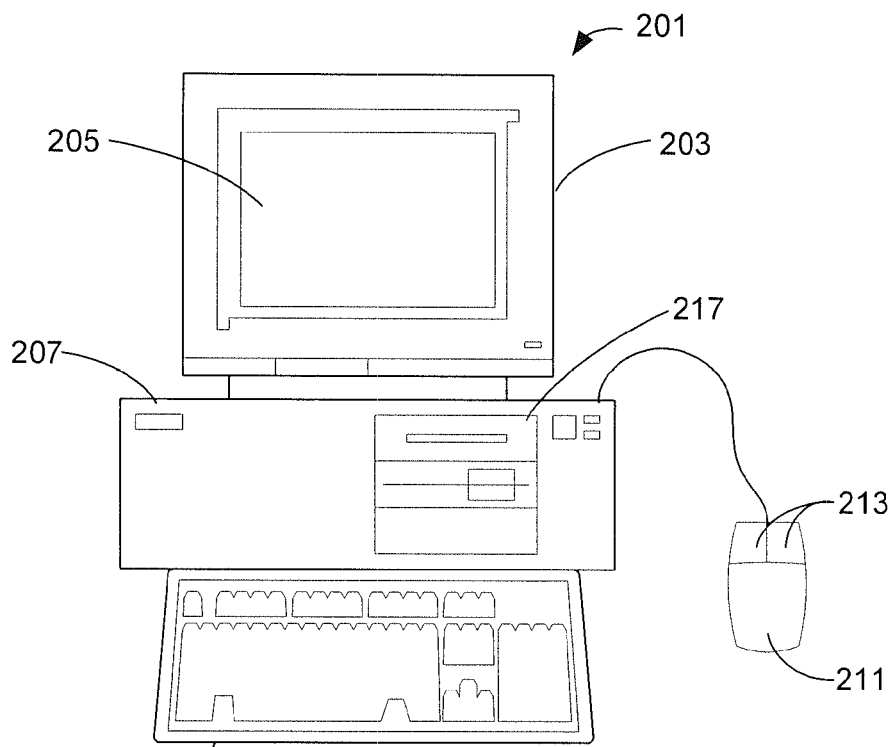
FIG. 2 shows a more detailed diagram of an exemplary client or computer which may be used in an implementation of the invention.

FIG. 2 shows an exemplary client or server system. In an embodiment, a user interfaces with the system through a computer workstation system, such as shown in FIG. 2. FIG. 2 shows a computer system 201 that includes a monitor 203, screen 205, cabinet 207, keyboard 209, and mouse 211. Mouse 211 may have one or more buttons such as mouse buttons 213. Cabinet 207 houses familiar computer components, some of which are not shown, such as a processor, memory, mass storage devices 217, and the like.

Mass storage devices 217 may include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc®), flash and other nonvolatile solid-state storage (e.g., USB flash drive), battery-backed-up volatile memory, tape storage, reader, and other similar media, and combinations of these.

A computer-implemented or computer-executable version of the invention may be embodied using, stored on, or associated with computer-readable medium or non-transitory computer-readable medium. A computer-readable medium may include any medium that participates in providing instructions to one or more processors for execution. Such a medium may take many forms including, but not limited to, nonvolatile, volatile, and transmission media. Nonvolatile media includes, for example, flash memory, or optical or magnetic disks. Volatile media includes static or dynamic memory, such as cache memory or RAM. Transmission media includes coaxial cables, copper wire, fiber optic lines, and wires arranged in a bus. Transmission media can also take the form of electromagnetic, radio frequency, acoustic, or light waves, such as those generated during radio wave and infrared data communications.

For example, a binary, machine-executable version, of the software of the present invention may be stored or reside in RAM or cache memory, or on mass storage device 217. The source code of the software may also be stored or reside on mass storage device 217 (e.g., hard disk, magnetic disk, tape, or CD-ROM). As a further example, code may be transmitted via wires, radio waves, or through a network such as the Internet.

Figure 3:
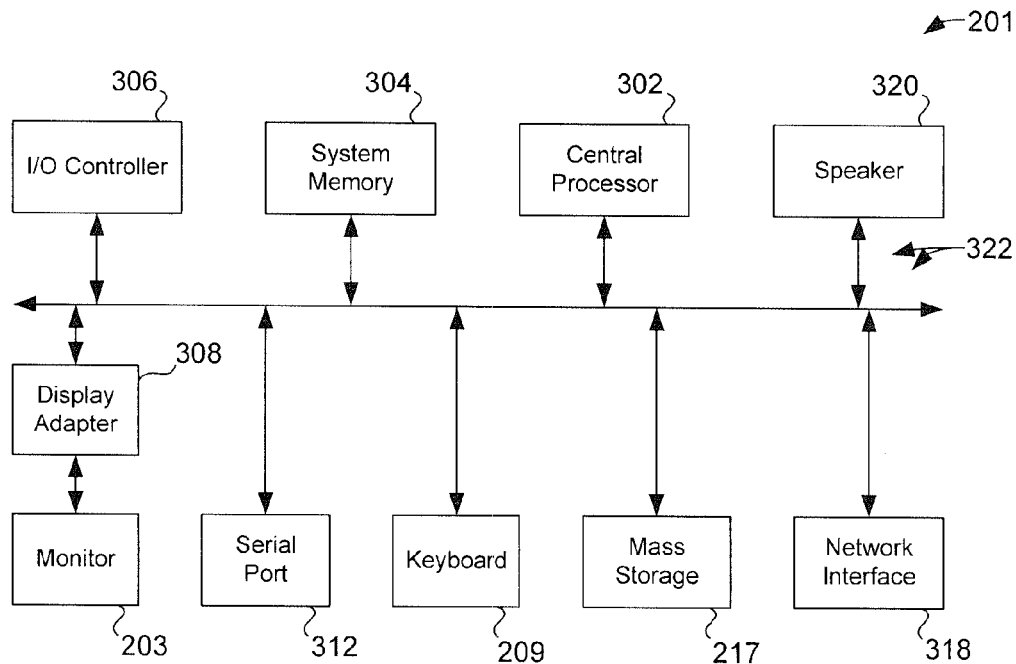
FIG. 3 shows a system block diagram of a client computer system.

FIG. 3 shows a system block diagram of computer system 201. As in FIG. 2, computer system 201 includes monitor 203, keyboard 209, and mass storage devices 217. Computer system 201 further includes subsystems such as central processor 302, system memory 304, input/output (I/O) controller 306, display adapter 308, serial or universal serial bus (USB) port 312, network interface 318, and speaker 320. In an embodiment, a computer system includes additional or fewer subsystems. For example, a computer system could include more than one processor 302 (i.e., a multiprocessor system) or a system may include a cache memory.

Arrows such as 322 represent the system bus architecture of computer system 201. However, these arrows are illustrative of any interconnection scheme serving to link the subsystems. For example, speaker 320 could be connected to the other subsystems through a port or have an internal direct connection to central processor 302. The processor may include multiple processors or a multicore processor, which may permit parallel processing of information. Computer system 201 shown in FIG. 2 is but an example of a suitable computer system. Other configurations of subsystems suitable for use will be readily apparent to one of ordinary skill in the art.

Computer software products may be written in any of various suitable programming languages, such as C, C++, C#, Pascal, Fortran, Perl, Matlab® (from MathWorks), SAS, SPSS, JavaScript®, AJAX, Java®, SQL, and XQuery (a query language that is designed to process data from XML files or any data source that can be viewed as XML, HTML, or both). The computer software product may be an independent application with data input and data display modules. Alternatively, the computer software products may be classes that may be instantiated as distributed objects. The computer software products may also be component software such as Java Beans® (from Oracle Corporation) or Enterprise Java Beans (EJB from Oracle Corporation). In a specific embodiment, the present invention provides a computer program product which stores instructions such as computer code to program a computer to perform any of the processes or techniques described.

An operating system for the system may be one of the Microsoft Windows® family of operating systems (e.g., Windows 95®, 98, Me, Windows NT®, Windows 2000®, Windows XP®, Windows XP® x64 Edition, Windows Vista®, Windows 7®, Windows CE®, Windows Mobile®), Linux, HP-UX, UNIX, Sun OS®, Solaris®, Mac OS X®, Alpha OS®, AIX, IRIX32, or IRIX64. Other operating systems may be used. Microsoft Windows® is a trademark of Microsoft® Corporation.

Furthermore, the computer may be connected to a network and may interface to other computers using this network. The network may be an intranet, internet, or the Internet, among others. The network may be a wired network (e.g., using copper), telephone network, packet network, an optical network (e.g., using optical fiber), or a wireless network, or any combination of these. For example, data and other information may be passed between the computer and components (or steps) of the system using a wireless network using a protocol such as Wi-Fi (IEEE standards 802.11, 802.11a, 802.11b, 802.11e, 802.11g, 802.11i, and 802.11n, just to name a few examples). For example, signals from a computer may be transferred, at least in part, wirelessly to components or other computers.

In an embodiment, with a Web browser executing on a computer workstation system, a user accesses a system on the World Wide Web (WWW) through a network such as the Internet. The Web browser is used to download web pages or other content in various formats including HTML, XML, text, PDF, and postscript, and may be used to upload information to other parts of the system. The Web browser may use uniform resource identifiers (URLs) to identify resources on the Web and hypertext transfer protocol (HTTP) in transferring files on the Web.

Figure 4:
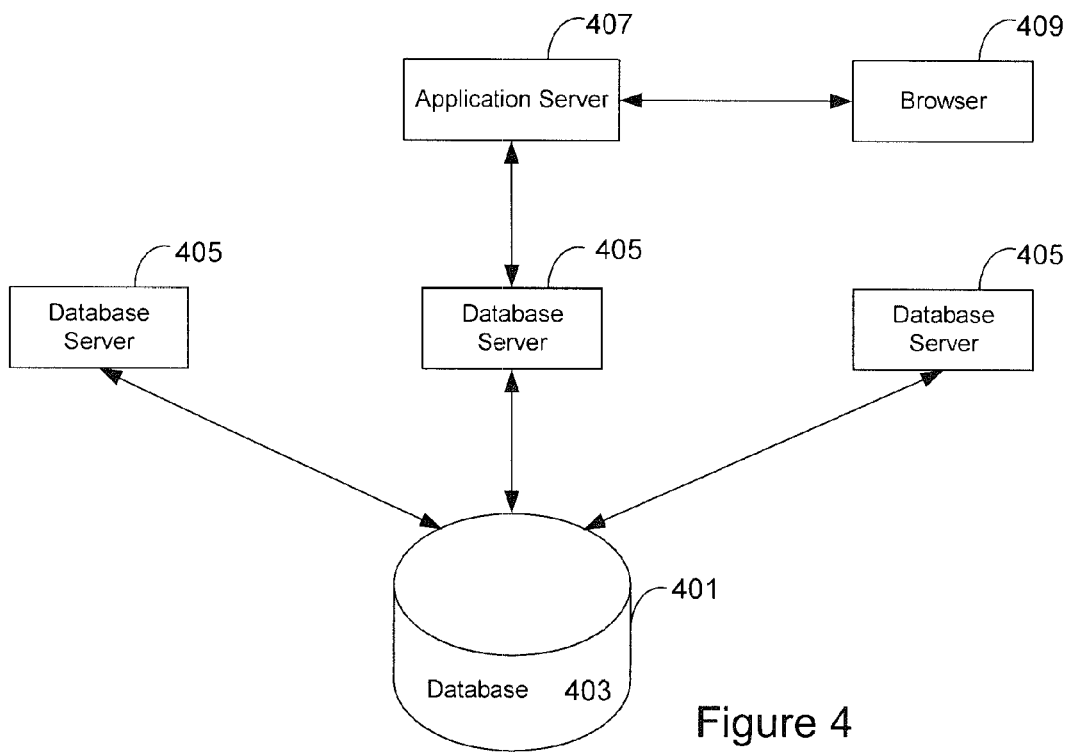
FIG. 4 shows a data source or data service in the form of a database system.

FIG. 4 shows a data source or data service in the form of a database system. A database may be part of a database management system. One suitable database management system architecture is a three-tiered architecture as shown.

In a first tier is the core of a database management system, a central storage 401 that holds or stores a database or repository 403. The database typically resides on one or more hard drives, and is generally part of a larger computer system. The information may be stored in the database in a variety of formats. An example is an Extensible Markup Language (XML) database. An XML database is a data persistence software system that allows data to be stored in XML format. Another example is a relational database management system (RDMS) which uses tables to store the information.

In a second tier are database servers 405. The database servers are instances of a program that interacts with the database. Each instance of a database server may, among other features, independently query the database and store information in the database. Depending on the implementation, the database servers 405 may or may not include user-friendly interfaces, such as graphical user interfaces.

In a third tier is an application server 407. There may be multiple application servers. In an implementation, the application server provides the user interfaces to the database servers. By way of example, the application server may be a web application server on the Internet or any other network. The application server may also be a virtual database server or a virtual directory server. The application server may provide user-friendly mechanisms and interfaces for accessing the database through the database servers. In an implementation, a web browser 409 is utilized to access the application server.

Figure 5:
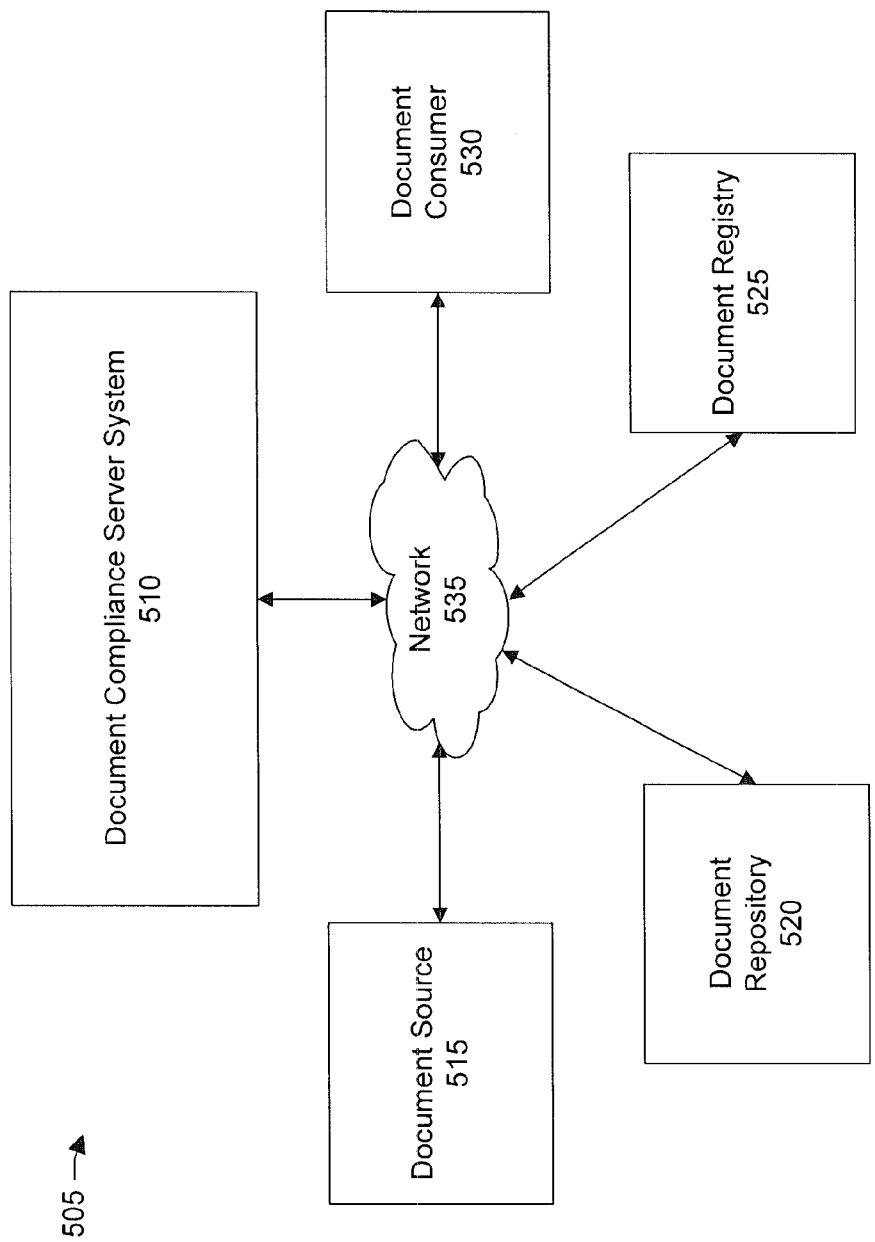
FIG. 5 shows a simplified block diagram of a document compliance system.

FIG. 5 shows a simplified block diagram of a computing architecture 505 incorporating a system for enabling legacy patients clinical documents for open sharing according to an embodiment of the present invention. This architecture includes a document compliance server system 510, a document source system component 515, a document repository system component 520, a document registry system component 525, and a document consumer system component 530, which are connected to a network 535.

The network allows the various systems to communicate and exchange information with each other. The network is as shown in FIG. 1 and described above. The various systems may include general purpose computers with hardware and software, such as shown in FIGS. 2-3 and described above.

In a specific embodiment, the document compliance system is implemented within a healthcare communication network and, more specifically, within a cross-enterprise document sharing ("XDS") infrastructure as specified by Integrating the Healthcare Enterprise ("IHE"). IHE is an initiative by healthcare professionals and industry to improve the way computer systems in healthcare share information. IHE promotes the coordinated use of established standards such as DICOM and HL7 to address specific clinical needs to improve patient care. This patent application discusses a document compliance system that allows legacy data to be integrated into an XDS infrastructure. It should be appreciated, however, that the document compliance system can be implemented in non-healthcare settings.

In this specific embodiment, the document source system is responsible for providing the clinical documents. Typically, a clinical document is associated with a patient or will include patient healthcare information. A clinical document may include, for example, patient demographic information (e.g., patient name, address, or phone number), a radiology report with or without referenced images, a pathology report, a discharge summary, a medication list, a lab report, health insurance information, or a diagnosis report—just to name a few examples.

The document repository is responsible for storing the clinical documents and forwarding document metadata to the document registry. The document registry is responsible for maintaining an index of published documents. The registry includes a set of document attributes or properties (i.e., metadata) for each document stored. Some examples of document attributes include patient name, document type, and storage location.

The document consumer uses the registry to search for the documents stored in the document repository. For example, the document consumer can query the registry and the registry will return a list of documents responsive to the query. From this list, the document consumer can select a document. The selected document is then transmitted from the document repository to the document consumer.

Each document stored in the document repository has a corresponding registration in the document registry so that the document can be searched. An XDS system requires that documents comply with certain standards before they can be stored in an XDS system. Specifically, the XDS system requires that the registration of the document include certain metadata information or attributes associated with the document. This can be problematic in cases where the organization (e.g., healthcare provider) wishes to integrate legacy documents into an XDS system because the legacy documents may not be XDS compliant. For example, an existing set of attributes associated with a legacy document may not include the XDS required metadata attributes, the existing set of attributes may not be in a format compatible with the XDS protocol, the existing set of attributes may include an attribute not permitted or allowed by the XDS system, or combinations of these. Table A below shows an example of a transaction formatted according to the XDS protocol. This example includes full metadata for the submission of a single document.

TABLE A

```
POST /tf6/services/xdsrepositoryb HTTP/1.1
Content-Type: multipart/related;
boundary=MIMEBoundaryurn_uuid_566EAD10FEBB55C5A61257193478449;
type="application/xop+xml";
start="<0.urn:uuid:566EAD10FEBB55C5A61257193478450@apache.org>"; start-
info="application/soap+xml"; action="urn:ihe:iti:2007:ProvideAndRegisterDocumentSet-b"
User-Agent: Axis2
Host: localhost:5000
--MIMEBoundaryurn_uuid_566EAD10FEBB55C5A61257193478449
Content-Type: application/xop+xml; charset=UTF-8; type="application/soap+xml"
Content-Transfer-Encoding: binary
Content-ID: <0.urn:uuid:566EAD10FEBB55C5A61257193478450@apache.org>
<?xml version='1.0' encoding='UTF-8'?>
<soapenv:Envelope xmlns:soapenv="http://www.w3.org/2003/05/soap-envelope"
    xmlns:wsa="http://www.w3.org/2005/08/addressing">
    <soapenv:Header>
        <wsa:To>http://localhost:5000/tf6/services/xdsrepositoryb</wsa:To>
        <wsa:MessageID>urn:uuid:566EAD10FEBB55C5A61257193478400</wsa:MessageID>
        <wsa:Action>urn:ihe:iti:2007:ProvideAndRegisterDocumentSet-b</wsa:Action>
    </soapenv:Header>
    <soapenv:Body>
        <xdsb:ProvideAndRegisterDocumentSetRequest xmlns:xdsb="urn:ihe:iti:xds-b:2007">
            <lcm:SubmitObjectsRequest xmlns:lcm="urn:oasis:names:tc:ebxml-
regrep:xsd:lcm:3.0">
                <rim:RegistryObjectList xmlns:rim="urn:oasis:names:tc:ebxml-regrep:xsd:
                rim:3.0">
                    <rim:ExtrinsicObject id="Document01" mimeType="text/plain"
                        objectType="urn:uuid:7edca82f-054d-47f2-a032-9b2a5b5186c1">
                        <rim:Slot name="creationTime">
                            <rim:ValueList>
                                <rim:Value>20051224</rim:Value>
                            </rim:ValueList>
                        </rim:Slot>
```

TABLE A-continued

```
            <rim:Slot name="languageCode">
                <rim:ValueList>
                    <rim:Value>en-us</rim:Value>
                </rim:ValueList>
            </rim:Slot>
            <rim:Slot name="serviceStartTime">
                <rim:ValueList>
                    <rim:Value>200412230800</rim:Value>
                </rim:ValueList>
            </rim:Slot>
            <rim:Slot name="serviceStopTime">
                <rim:ValueList>
                    <rim:Value>200412230801</rim:Value>
                </rim:ValueList>
            </rim:Slot>
            <rim:Slot name="sourcePatientId">
                <rim:ValueList>
                    <rim:Value>89765a87b^^^&3.4.5&ISO</rim:Value>
                </rim:ValueList>
            </rim:Slot>
            <rim:Slot name="sourcePatientInfo">
                <rim:ValueList>
                    <rim:Value>PID-3|pid1^^^&1.2.3&ISO</rim:Value>
                    <rim:Value>PID-5|Doe^John^^^</rim:Value>
                    <rim:Value>PID-7|19560527</rim:Value>
                    <rim:Value>PID-8|M</rim:Value>
                    <rim:Value>PID-11|100 Main St^^Metropolis^Il^44130^USA</rim:Value>
                </rim:ValueList>
            </rim:Slot>
            <rim:Name>
                <rim:LocalizedString value="Physical"/>
            </rim:Name>
            <rim:Description>
            <rim:Classification
                classificationScheme="urn:uuid:93606bcf-9494-43ec-9b4e-a7748d1a838d"
                classifiedObject="Document01" nodeRepresentation=""
                objectType="urn:oasis:names:tc:ebxml-
regrep:ObjectType:RegistryObject:Classification"
                id="id_1">
                <rim:Slot name="authorPerson">
                    <rim:ValueList>
                        <rim:Value>^Smitty^Gerald^^^</rim:Value>
                    </rim:ValueList>
                </rim:Slot>
                <rim:Slot name="authorInstitution">
                    <rim:ValueList>
                        <rim:Value>Cleveland Clinic</rim:Value>
                        <rim:Value>Parma Community</rim:Value>
                    </rim:ValueList>
                </rim:Slot>
                <rim:Slot name="authorRole">
                    <rim:ValueList>
                        <rim:Value>Attending</rim:Value>
                    </rim:ValueList>
                </rim:Slot>
                <rim:Slot name="authorSpecialty">
                    <rim:ValueList>
                        <rim:Value>Orthopedic</rim:Value>
                    </rim:ValueList>
                </rim:Slot>
            </rim:Classification>
            <rim:Classification
                classificationScheme="urn:uuid:93606bcf-9494-43ec-9b4e-a7748d1a838d"
                classifiedObject="Document01" nodeRepresentation=""
                objectType="urn:oasis:names:tc:ebxml-
regrep:ObjectType:RegistryObject:Classification"
                id="id_2">
                <rim:Slot name="authorPerson">
                    <rim:ValueList>
                        <rim:Value>^Dopplemeyer^Sherry^^^</rim:Value>
                    </rim:ValueList>
                </rim:Slot>
                <rim:Slot name="authorInstitution">
                    <rim:ValueList>
                        <rim:Value>Cleveland Clinic</rim:Value>
                        <rim:Value>Berea Community</rim:Value>
                    </rim:ValueList>
                </rim:Slot>
                <rim:Slot name="authorRole">
                    <rim:ValueList>
```

TABLE A-continued

```
            <rim:Value>Primary Surgon</rim:Value>
          </rim:ValueList>
        </rim:Slot>
        <rim:Slot name="authorSpecialty">
          <rim:ValueList>
            <rim:Value>Orthopedic</rim:Value>
          </rim:ValueList>
        </rim:Slot>
      </rim:Classification>
      <rim:Classification
        classificationScheme="urn:uuid:41a5887f-8865-4c09-adf7-e362475bl43a"
        classifiedObject="Document01" nodeRepresentation="History and Physical"
        objectType="urn:oasis:names:tc:ebxml-
regrep:ObjectType:RegistryObject:Classification"
        id="id_3">
        <rim:Slot name="codingScheme">
          <rim:ValueList>
            <rim:Value>Connect-a-thon classCodes</rim:Value>
          </rim:ValueList>
        </rim:Slot>
        <rim:Name>
          <rim:LocalizedString value="History and Physical"/>
        </rim:Name>
      </rim:Classification>
      <rim:Classification
        classificationScheme="urn:uuid:f4f85eac-e6cb-4883-b52442705394840f"
        classifiedObject="Document01"
        nodeRepresentation="1.3.6.1.4.1.21367.2006.7.101"
        objectType="urn:oasis:names:tc:ebxml-
regrep:ObjectType:RegistryObject:Classification"
        id="id_4">
        <rim:Slot name="codingScheme">
          <rim:ValueList>
            <rim:Value>Connect-a-thon confidentialityCodes</rim:Value>
          </rim:ValueList>
        </rim:Slot>
        <rim:Name>
          <rim:LocalizedString value="Clinical-Staff"/>
        </rim:Name>
      </rim:Classification>
      <rim:Classification
        classificationScheme="urn:uuid:a09d5840-386c-46f2-b5ad-9c3699a4309d"
        classifiedObject="Document01" nodeRepresentation="CDAR2/IHE 1.0"
        objectType="um:oasis:names:tc:ebxml-
regrep:ObjectType:RegistryObject:Classification"
        id="id_5">
        <rim:Slot name="codingScheme">
          <rim:ValueList>
            <rim:Value>Connect-a-thon formatCodes</rim:Value>
          </rim:ValueList>
        </rim:Slot>
        <rim:Name>
          <rim:LocalizedString value="CDAR2/IHE 1.0"/>
        </rim:Name>
      </rim:Classification>
      <rim:Classification
        classificationScheme="urn:uuid:f33fb8ac-18af-42cc-ae0e-ed0b0bdb91e1"
        classifiedObject="Document01" nodeRepresentation="Outpatient"
        objectType="urn:oasis:names:tc:ebxml-
regrep:ObjectType:RegistryObject:Classification"
        id="id_6">
        <rim:Slot name="codingScheme">
          <rim:ValueList>
            <rim:Value>Connect-a-thon
              healthcareFacilityTypeCodes</rim: Value>
          </rim:ValueList>
        </rim:Slot>
        <rim:Name>
          <rim:LocalizedString value="Outpatient"/>
        </rim:Name>
      </rim:Classification>
      <rim:Classification
        classificationScheme="urn:uuid:cccf5598-8b07-4b77-a05e-ae952c785ead"
        classifiedObject="Document01" nodeRepresentation="General Medicine"
        objectType="urn:oasis:names:tc:ebxml-
regrep:ObjectType:RegistryObject:Classification"
        id="id_7">
        <rim:Slot name="codingScheme">
          <rim:ValueList>
            <rim:Value>Connect-a-thon practiceSettingCodes</rim:Value>
```

TABLE A-continued

```
          </rim:ValueList>
        </rim:Slot>
        <rim:Name>
          <rim:LocalizedString value="General Medicine"/>
        </rim:Name>
      </rim:Classification>
      <rim:Classification
          classificationScheme="urn:uuid:f0306f51-975f-434e-a61c-c59651d33983"
          classifiedObject="Document01" nodeRepresentation="34108-1"
          objectType="urn:oasis:names:tc:ebxml-
regrep:ObjectType:RegistryObject:Classification"
          id="id_8">
        <rim:Slot name="codingScheme">
          <rim:ValueList>
            <rim:Value>LOINC</rim:Value>
          </rim:ValueList>
        </rim:Slot>
        <rim:Name>
          <rim:LocalizedString value="Outpatient Evaluation And Management"/>
        </rim:Name>
      </rim:Classification>
      <rim:ExternalIdentifier
          identificationScheme="urn:uuid:58a6f841-87b3-4a3e-92fd-a8ffeff98427"
          value="76cc765a442f410^^^&1.3.6.1.4.1.21367.2005.3.7&ISO"
          objectType="urn:oasis:names:tc:ebxml-
regrep:ObjectType:RegistryObject:ExternalIdentifier"
          id="id_9" registryObject="Document01">
        <rim:Name>
          <rim:LocalizedString value="XDSDocumentEntry.patientId"/>
        </rim:Name>
      </rim:ExternalIdentifier>
      <rim:ExternalIdentifier
          identificationScheme="urn:uuid:2e82c1f6-a085-4c72-9da3-8640a32e42ab"
          value="2009.9.1.2455"
          objectType="urn:oasis:namesnc:ebxml-
regrep:ObjectType:RegistryObject:ExternalIdentifier"
          id="id_10" registryObject="Document01">
        <rim:Name>
          <rim:LocalizedString value="XDSDocumentEntry.uniqueId"/>
        </rim:Name>
      </rim:ExternalIdentifier>
    </rim:ExtrinsicObject>
    <rim:RegistryPackage id="SubmissionSet01"
        objectType="urn:oasis:names:tc:ebxml-
regrep:ObjectType:RegistryObject:RegistryPackage">
      <rim:Slot name="submissionTime">
        <rim:ValueList>
          <rim:Value>20041225235050</rim:Value>
        </rim:ValueList>
      </rim:Slot>
      <rim:Name>
        <rim:LocalizedString value="Physical"/>
      </rim:Name>
      <rim:Description>
        <rim:LocalizedString value="Annual physical"/>
      </rim:Description>
      <rim:Classification
          classificationScheme="urn:uuid:a7058bb9-b4e4-4307-ba5b-e3f0ab85e12d"
          classifiedObject="SubmissionSet01" nodeRepresentation=""
          objectType="urn:oasis:names:tc:ebxml-
regrep:ObjectType:RegistryObject:Classification"
          id="id_11">
        <rim:Slot name="authorPerson">
          <rim:ValueList>
            <rim:Value>^Dopplemeyer^Sherry^^^</rim:Value>
          </rim:ValueList>
        </rim:Slot>
        <rim:Slot name="authorInstitution">
          <rim:ValueList>
            <rim:Value>Cleveland Clinic</rim:Value>
            <rim:Value>Berea Community</rim:Value>
          </rim:ValueList>
        </rim:Slot>
        <rim:Slot name="authorRole">
          <rim:ValueList>
            <rim:Value>Primary Surgeon</rim:Value>
          </rim:ValueList>
        </rim:Slot>
        <rim:Slot name="authorSpecialty">
          <rim:ValueList>
```

TABLE A-continued

```
            <rim:Value>Orthopedic</rim:Value>
          </rim:ValueList>
        </rim:Slot>
      </rim:Classification>
      <rim:Classification
          classificationScheme="urn:uuid:aa543740-bdda-424e-8c96-df4873be8500"
          classifiedObject="SubmissionSet01"
          nodeRepresentation="History and Physical"
          objectType="urn:oasis:names:tc:ebxml-
regrep:ObjectType:RegistryObject:Classification"
          id="id_12">
        <rim:Slot name="codingScheme">
          <rim:ValueList>
            <rim: Value>Connect-a-thon contentTypeCodes</rim:Value>
          </rim:ValueList>
        </rim:Slot>
        <rim:Name>
          <rim:LocalizedString value="History and Physical"/>
        </rim:Name>
      </rim:Classification>
      <rim:ExternalIdentifier
          identificationScheme="urn:uuid:96fdda7c-d067-4183-912e-bf5ee74998a8"
          value="2009.9.1.2456"
          objectType="urn:oasis:names:tc:ebxml-
regrep:ObjectType:RegistryObject:ExternalIdentifier"
          id="id_13"registryObject="SubmissionSet01">
        <rim:Name>
          <rim:LocalizedString value="XDSSubmissionSet.uniqueId"/>
        </rim:Name>
      </rim:ExternalIdentifier>
      <rim:ExternalIdentifier
          identificationScheme="urn:uuid:554ac39e-e3fe-47fe-b233-965d2a147832"
          value="1.3.6.1.4.1.21367.2009.1.2.1"
          objectType="urn:oasis:names:tc:ebxml-
regrep:ObjectType:RegistryObject:ExternalIdentifier"
          id="id_14"registryObject="SubmissionSet01">
        <rim:Name>
          <rim:LocalizedString value="XDSSubmissionSet.sourceId"/>
        </rim:Name>
      </rim:ExternalIdentifier>
      <rim:ExternalIdentifier
          identificationScheme="urn:uuid:6b5aeala-874d-4603-a4bc-96a0a7b38446"
          value="76cc765a442f410^^^&1.3.6.1.4121367.2005.3.7&ISO"
          objectType="urn:oasis:names:tc:ebxml-
regrep:ObjectType:RegistryObject:ExternalIdentifier"
          id="id_15" registryObject="SubmissionSet01">
        <rim:Name>
          <rim:LocalizedString value="XDSSubmissionSet.patientId"/>
        </rim:Name>
      </rim:ExternalIdentifier>
    </rim:RegistryPackage>
    <rim:Classification classifiedObject="SubmissionSet01"
        classificationNode="urn:uuid:a54d6aa5-d40d-43f9-88c5-b4633d873bdd"
        id="ID_1216346_1"
        objectType="urn:oasis:names:tc:ebxml-
regrep:ObjectType:RegistryObject:Classification"/>
    <rim:Association
        associationType="urn:oasis:names:tc:ebxml-
regrep:AssociationType:HasMember"
        sourceObject="SubmissionSet01"targetObject="Document01"
id="ID_1216346_2"
        objectType="urn:oasis:names:tc:ebxml-
regrep:ObjectType:RegistryObject:Association">
      <rim:Slot name="SubmissionSetStatus">
        <rim:ValueList>
          <rim:Value>Original</rim:Value>
        </rim:ValueList>
      </rim:Slot>
    </rim:Association>
  </rim:RegistryObjectList>
 </lcm:SubmitObjectsRequest>
 <xdsb:Documentid="Document01">
   <xop:Include
href="cid:1.urn:uuid:566EAD1OFEBB55C5A61257193478499@apache.org"
        xmlns:xop="http://www.w3.org/2004/08/xop/include"/>
  </xdsb:Document>
    </xdsb:ProvideAndRegisterDocumentSetRequest>
  </soapenv:Body>
 </soapenv:Envelope>
--MIMEBoundaryurn_uuid_566EAD10FEBB55C5A61257193478449
```

TABLE A-continued

```
Content-Type:text/plain
Content-Transfer-Encoding:binary
Content-ID: <1.urn:uuid:566EAD10FEBB55C5A61257193478499@apache.org>
This is my document.
It is great!
--MIMEBoundaryurn_uuid_566EAD10FEBB55C5A61257193478449--
```

More particularly, healthcare data has long been paper intensive and estimates indicate that about 70-80 percent of the patient data are unstructured. Current efforts to eliminate paper and move into the era of open sharing do not easily address the question of what if anything can be done to bring these legacy documents online. This patent application describes systems and techniques to enable existing electronic data about the patient to be compliant with the current set of standards proposed by Integrating Health Enterprises ("IHE") and can also be extended to other versions of the standards as they evolve.

Metadata information may be captured along with its associated content and data extracted from it using optical character recognition or other process. The data may be stored in a database to facilitate structured searching. The information captured is linked to a patient record usually associated with the patient Medical Record Number. To enable legacy data to be included and displayed in a modern electronic health record ("EHR") that complies with the IHE standards, a feature of the system embellishes the legacy data with the required XDS data.

The metadata information may be stored separately from the document content or scanned document image. The metadata may be stored in or using software that assists in fast searches and gets a link to the content. For example, an MS Word document may have an author attribute. The author attribute may be saved or put into a RDBMS so that it can be easily looked up. Alternatively, the metadata information may be stored together with the document content. For example, DICOM structured reports puts an envelop around the document with the necessary metadata and transfers the metadata and the content as one unit.

In a specific implementation, the data is obtained through one or more of the following techniques. The unstructured content present along with the legacy data in the form of a document/image, etc. can be mined again and OCR'd in the case of images for data that can be used to embellish the existing data with attributes that it contains. In cases when the data cannot be used directly, it can be mapped to the required data through transformation tables. This approach is viable because in many cases the forms that are scanned follow a structured pattern, are usually specific to a diagnosis that is either bar coded on the form and in combination with the encounter ID can be used to reasonably infer some of the data required.

In this specific implementation, data required for the transformation can also be acquired from integrating with an external system and providing context like the patient ID, etc. to get the required information. Integrating data from disparate systems may be done in a Healthcare IT setting by using software frameworks such as Apache Camel to facilitate the integration. Some examples of an external system include an Enterprise Master Patient Index, a HIS system that gives us information given a patient Medical Record Number (MRN), and the like.

In this specific implementation, as a last resort data required may be provided by an end-user who inputs the necessary data. The process of getting the required metadata can be coordinated through a business process. Legacy data to be updated with the attributes required for conformance can be routed through a series of steps in an workflow where the first step mines for data within the document, the second step, using web services, gets the data from external system and as a last step a form can be presented to the user to validate or provide the needed metadata.

Table B below shows an example of some of the attributes that may or may not be required by an XDS infrastructure.

TABLE B

| Attribute | Description |
| --- | --- |
| author | Represents the humans and/or machines that authored the document. This attribute contains the following sub-attributes: authorInstitution authorPerson authorRole authorSpecialty |
| authorInstitution (sub-attribute of author) | Represents a specific healthcare facility under which the human and/or machines authored the document. A specific case is that of homecare. |
| authorPerson (sub-attribute of author) | Represents the humans and/or machines that authored the document within the authorInstitution. The document author may be the patient itself. |
| authorRole (sub-attribute of author) | A code that represents the role of the author with respect to the patient when the document was created. |
| authorSpecialty (sub-attribute of author) | Represents a specific specialty within a healthcare facility under which the human and/or machines authored the document. |
| availabilityStatus | An XDS Document shall have one of two availability statuses: Approved available for patient care Deprecated obsolete This attribute is always set to Approved as part of the submission of new XDS Documents. It may be changed to Deprecated under the primary responsibility of the Document Source with possible patient supervision. |

TABLE B-continued

| Attribute | Description |
| --- | --- |
| classCode | The code specifying the particular kind of document (e.g., Prescription, Discharge Summary, Report). |
| classCode DisplayName | The name to be displayed for communicating to a human the meaning of the classCode. |
| comments | Comments associated with the Document. |
| confidentialityCode | The code specifying the level of confidentiality of the XDS Document. |
| creationTime | Represents the time the author created the document in the Document Source. |
| entryUUID | This globally unique identifier is primarily intended for use as a document registry management identifier. |
| eventCodeList | This list of codes represents the main clinical acts, such as a colonoscopy or an appendectomy, being documented. |
| eventCodeListDisplay Name | The list of names to be displayed for communicating to human reader the meaning of the eventCode. |
| formatCode | Code globally uniquely specifying the format of the document. |
| formatCodeDisplayName | The name to be displayed for communicating to human reader the meaning of the formatCode. |
| hash | Hash key of the XDS Document itself. This value is computed by the Document Repository and used by the Document Registry for detecting the improper resubmission of XDS Documents. |
| healthcareFacility TypeCode | This code represents the type of organizational setting of the clinical encounter during which the documented act occurred. |
| healthcareFacility TypeCodeDisplay Name | The name to be displayed for communicating to a human the meaning of the healthcareFacilityTypeCode. |
| homeCommunityId | A globally unique identifier for a community. |
| languageCode | Specifies the human language of character data in the document. |
| legalAuthenticator | Represents a participant who has legally authenticated or attested the document within the authorInstitution. |
| mimeType | MIME type of the document in the Repository. |
| patientId | The patientId represents the subject of care of the document. |
| practiceSettingCode | The code specifying the clinical specialty where the act that resulted in the document was performed (e.g., Family Practice, Laboratory, Radiology). |
| practiceSettingCode DisplayName | The name to be displayed for communicating to a human the meaning of the practiceSettingCode. |
| repositoryUniqueId | The globally unique identifier of the repository where the document is stored, assigned by the Document Repository. This unique identifier for the Document Repository may be used to identify and connect to the specific Document Repository where the document is stored once its metadata has been retrieved from a Document Registry. |
| serviceStartTime | Represents the start time the service being documented took place. |
| serviceStopTime | Represents the stop time the service being documented took place |
| size | Size in bytes of the byte stream that was provided in the Register and Provide Transaction and stored by the XDS Document Repository. |
| sourcePatientId | The sourcePatientId represents the subject of care medical record Identifier (e.g., Patient Id) in the local patient Identifier Domain of the Document Source. |
| sourcePatientInfo | This attribute should contain demographics information of the patient to whose medical record this document belongs. This information typically includes: the patient first and last name, sex, and birth date. |
| title | Represents the title of the document. |
| typeCode | The code specifying the precise kind of document (e.g., Pulmonary History and Physical, Discharge Summary, Ultrasound Report). |
| typeCodeDisplay Name | The name to be displayed for communicating to a human the meaning of the typeCode. |
| uniqueId | The globally unique identifier assigned by the document creator to this document. |
| URI | For XDM the URI element shall point to the file containing the document. |

The "IHE IT Infrastructure Technical Framework Volume 3 (ITI TF-3) Cross-Transaction Specifications and Content Specifications" Revision 8.0-Final Text, Aug. 19, 2011" by IHE International, Inc., which is incorporated by reference, provides a further discussion of the attributes that may be required to register a document in an XDS system.

In a specific implementation, integrating legacy patient clinical documents into an XDS infrastructure may include removing, deleting, or not registering an exiting metadata attribute. For example, the existing metadata attribute may not be allowed or may not comply with the standard. In this specific implementation, a method includes reviewing a set of existing attributes associated with a document, determining that a first attribute of the set of existing attributes is not allowed by a document registry, determining that a second attribute of the set of existing attributes is allowed by the document repository, creating a set of compatible attributes allowed by the document registry, where the set of compatible attributes does not include the first attribute and includes the second attribute, transmitting the set of compatible attributes and the document to a document repository, where the document repository forwards the set of compatible attributes to the document registry for storage of the set of compatible attributes at the document registry, and the document is stored at the document repository separate from the set of compatible attributes.

In this specific implementation, a number of attributes in the set of existing attributes may be different from a number of attributes in the set of compatible attributes. The number of attributes in the set of compatible attributes may be less than, greater than, or equal to the number of attributes in the set of existing attributes. The number may be less than if, for example, the set of existing attributes includes an attribute not allowed by the registry. The number may be greater than if, for example, the set of existing attributes is missing an attribute required by the registry. The number may be equal to if, for example, each attribute in the set of existing attributes is allowed by the registry and there are no missing attributes.

Figure 6:
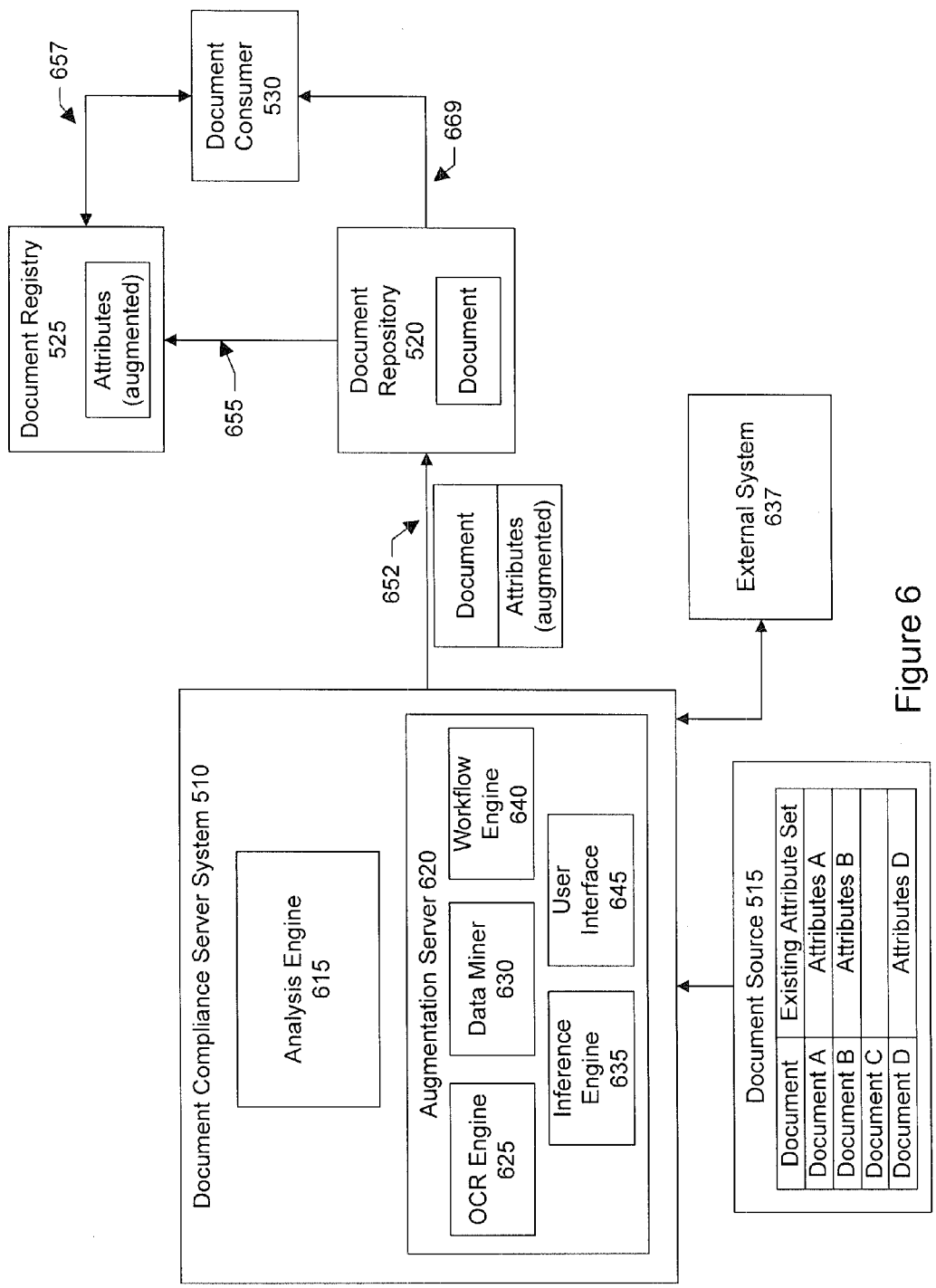
FIG. 6 shows a more detailed block diagram of the diagram shown in FIG. 5.

FIG. 6 shows a more detailed block diagram of the diagram shown in FIG. 5. In a specific implementation, document source 515 stores legacy data 605 in a database 610. The database may include a document and information associated with or about the document, i.e., metadata or a set of existing attributes. For example, as shown in FIG. 6, the database includes a document A having existing attribute set A, a document B having existing attribute set B, and a document D having existing attribute set D.

In the example shown in FIG. 6, the existing attributes sets are stored in fields separate from fields storing the documents. For example, the field storing the document may be storing a scanned document image and an existing attribute may be stored in a different field. In some cases, a document, such as a document C, may be stored in the database without having a set of existing attributes stored in a separate database field.

The documents stored in database 610 may be digital or scanned images of paper-based documents, documents originating in electronic form, or both. For example, a document stored in database 610 may be formatted as a portable document format ("PDF" file), an image file, a Tagged Image File Format ("TIFF" file), a Joint Photographic Experts Group ("JPEG" file), a text file, a Digital Imaging and Communications in Medicine ("DICOM" file), or Health Level 7 ("HL7") file format.

The set of attributes associated with a document may be referred to as metadata. Metadata includes information about the document. For example, the metadata may include information about the patient that is the subject of the document (e.g., patient name, age, gender, or mother's maiden name), information identifying the medical equipment (e.g., imaging machine) used to generate the document, the facility or hospital at which the document originated, the document author, the date of service, the document type, and so forth.

Table C below shows an example of some of the metadata attribute information that may be associated with a document.

TABLE C

| Attribute Field Name | Description |
|---|---|
| Patient name | General demographic information. |
| Previously registered name/maiden name | |
| Individual identifier/medical record number | |
| Universal patient health number | |
| Gender | |
| Race | |
| Address | |
| Telephone number | |
| Date of birth | |
| Organization | |
| Admission date | |
| Discharge date | |
| Legal authenticator | |
| Authentication date | |
| Transcriptionist/data enterer | |
| Transcription date | |
| Source of payment | |
| Chief complaint | The reason for the visit. |
| Symptom(s) | History of present illness |
| Onset of symptom(s) | |
| Duration of symptom(s) | |
| Over-the-counter (OTC) treatment | |
| Condition type | Past medical history |
| Date diagnosed | |
| Age of onset | |
| Treatment | |
| Condition status | |
| Drug | Medications |
| Dosage | |
| Route | |
| Quantity number | |
| Quantity form | |
| Frequency | |
| Start date | |
| Stop date | |
| Prescribed by | |
| Prescription date | |
| Prescription number | |
| Pharmacy | |
| Allergic reaction | |
| Source of medication list | |

TABLE C-continued

| Attribute Field Name | Description |
| --- | --- |
| Allergy or sensitivity type<br>Reaction<br>Severity<br>Date last occurred<br>Treatment | Allergies, adverse reactions, and alerts that are pertinent to the patient's current or past medical history. |
| Marital status<br>Occupation<br>Home environment<br>Daily routine<br>Dietary patterns<br>Sleep patterns<br>Exercise patterns<br>Coffee consumption<br>Tobacco use<br>Alcohol use<br>Drug use | Social history, the patient's occupational, personal (i.e., lifestyle), social, and environmental history and health risk factors, administrative data such as marital status, race, ethnicity, and religious affiliation. |
| Child health history<br>Adult health history<br>Hereditary diseases<br>Mother health status<br>Mother age of death<br>Mother cause of death<br>Father health status<br>Father age of death<br>Father cause of death<br>Sibling(s) health status<br>Sibling(s) age of death<br>Sibling(s) cause of death | Family history, the patient's genetic relatives in terms of relevant health risk factors that have a potential impact on the patient's healthcare profile. |
| Pulse<br>Respiratory rate<br>Systolic blood pressure<br>Diastolic blood pressure<br>Body temperature<br>Height<br>Weight<br>Body mass index<br>Head circumference<br>Crown-to-rump length<br>Pulse oximetry | Physical examination, patient vital signs. |
| Appearance<br>Body build<br>Demeanor<br>Hygiene | Patient's general appearance. |
| Skin<br>Head<br>Eyes<br>Ears<br>Nose and sinus<br>Mouth and throat<br>Neck<br>Thorax, anterior, and posterior<br>Breasts<br>Lungs<br>Cardiovascular<br>Abdomen<br>Male genitourinary<br>Female reproductive organs<br>Ano-rectal<br>Musculoskeletal system<br>Extremities<br>Lymphatics<br>Peripheral vascular<br>Neurologic<br>Mental status | Physically observed findings. |
| Test<br>Result/finding<br>Result/finding date<br>Interpretation | Diagnostic findings, observations generated by laboratories, imaging procedures, and other procedures. |
| Diagnoses<br>Disposition | Treatment recommendations. |
| Procedure<br>Date<br>Physician<br>Institution/location<br>Result | Procedure history |

TABLE C-continued

| Attribute Field Name | Description |
| --- | --- |
| Vaccine | Immunizations |
| Vaccine type | |
| Dose | |
| Age administered | |
| Date administered | |
| Lot number | |
| Physician | |
| Final diagnosis | Patient's condition on discharge |
| Condition on discharge | |
| Reason for discharge | |
| Disposition patient instructions | Discharge instructions |
| Follow-up action | |
| Follow-up target date | |
| Surgeon | Operative staff, clinicians who were present for the procedure such as who performed the surgery and who assisted. |
| Assistant | |
| Anesthesiologist | |
| Preoperative diagnoses | Operative diagnoses of the patient prior to the surgery, after the surgery, or both. |
| Postoperative diagnoses | |
| Operation/procedures performed | How the surgery was performed, what equipment was used/implanted including bandages and sutures, and what was concluded about patient diagnoses based on findings, and an identification of complications during surgery. |
| Operation description | |
| Findings | |
| Sedation/anesthesia | |
| Complications | |
| Drains | |
| Estimated blood loss | |
| Packs | |
| Sutures | |
| Patient condition | Patient's status after surgery and any precautions that need to be taken for recovery. |
| Discharge from recovery care | |

It should be appreciated that a set of attributes associated with a document may not include each of the attributes listed in the table above. A set of attributes associated with a document may include a subset of the listed attributes, or one or more other attributes not listed in the table above.

As shown in FIG. 6, document compliance server system 510 includes an analysis engine 615 and an augmentation server 620. In a specific implementation, the augmentation server includes an optical character recognition ("OCR") engine 625, a data miner 630, an inference engine 635, a workflow engine 640, and a user interface 645.

The analysis engine is responsible for analyzing documents from document source 515 to determine whether the documents are XDS complaint. The analysis engine may identify a document as being XDS compliant if an existing set of attributes associated with a document includes the attributes required by the XDS document registry, the attributes are formatted according to the XDS protocol, or both.

If the analysis engine determines that a document is standards compliant (e.g., XDS compliant), the document including the set of attributes or metadata information associated with the document, is transmitted to the document repository. The document repository stores the document at the repository and forwards the attributes to the document registry for storage of the attributes at the document registry. In a specific implementation, a user may flag or select which documents in database 610 should be standards (e.g., XDS) enabled. In this specific implementation, the analysis engine scans the database and retrieves the flagged documents and associated attributes (if any) for a standards (e.g., XDS) compliancy analysis.

If the analysis engine determines that a document is not standards compliant (e.g., XDS compliant), the document, existing set of attributes, or both are provided to the augmentation server. The augmentation server is responsible for obtaining the required attributes for the document to be standards (e.g., XDS) enabled or capable of being stored in standard (e.g., an XDS) system before the document is provided to the document repository. Upon the existing set of attributes being augmented with the required attributes, formatted according to the standards (e.g., XDS) protocol, or both, the document and augmented attributes are transmitted 652 to the document repository. As discussed above, the repository forwards 655 the attributes to the document registry and the document is stored at the repository. The document consumer can query 657 the registry. The registry returns a result responsive to the query that includes a reference or pointer to the location of the document on the repository. The user can select the document from the query result and the repository provides 669 the document to the consumer.

The augmentation server may use any technique or combination of techniques for obtaining the attributes. The workflow engine is responsible for coordinating the different techniques for obtaining the attributes. In brief, a first technique includes examining the document content for the required attributes. The document may be processed by the OCR engine to generate OCR data. The data miner mines the OCR data to search for or find the required metadata attributes. The interference engine may infer the attributes by evaluating user-configurable rules. A second technique may include retrieving the required attributes from an external system 637. A third technique may include prompting the user through the user interface to input the required attributes.

Figure 7:
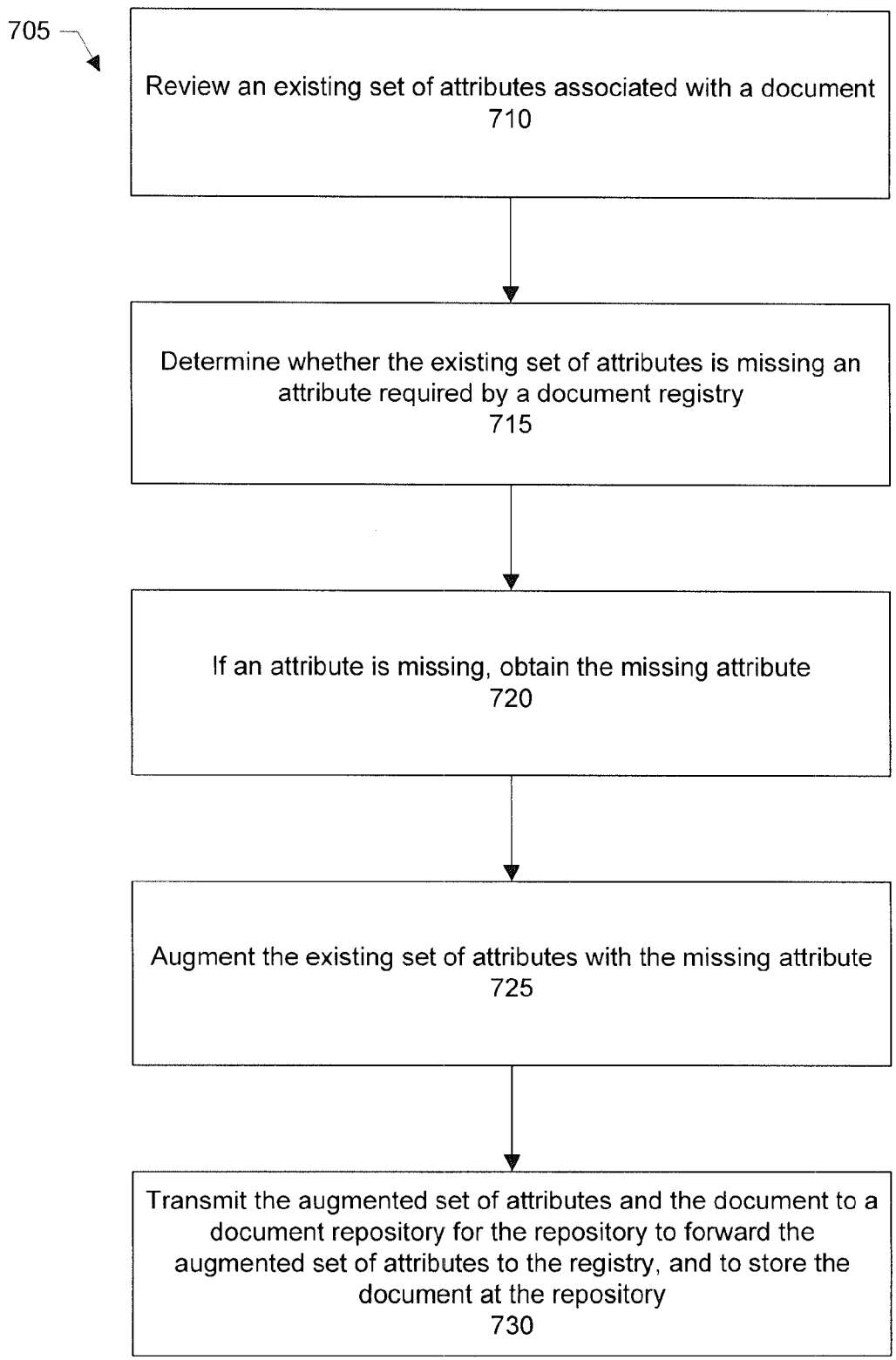
FIG. 7 shows an overall flow for augmenting a set of existing document attributes.

FIG. 7 shows an overall flow 705 for enabling legacy patient clinical documents for open sharing. Some specific flows are presented in this application, but it should be understood that the process is not limited to the specific flows and steps presented. For example, a flow may have additional steps (not necessarily described in this application), different steps which replace some of the steps presented, fewer steps or a subset of the steps presented, or steps in a different order than presented, or any combination of these. Further, the steps in other implementations may not be exactly the same as the steps presented and may be modified or altered as appropriate for a particular process, application or based on the data.

In a step 710, the document compliance system reviews a set of existing attributes associated with a document. In a specific implementation, the system stores a set or a list of attributes required by an XDS document registry. The analysis server compares the set of required attributes with a set of existing attributes associated with a legacy document. If each attribute from the set of required attributes has a corresponding or matching attribute from the set of existing attributes, the analysis server may determine that the document is XDS compliant.

For example, the set of required attributes may include attribute fields such as "author," "patient name," "classification code," "hospital," and "practice heading." If each of these fields can be found in the set of existing attributes, the analysis server may determine that the document is XDS compliant.

In a step 715, if each attribute from the set of required attributes does not have a corresponding or matching attribute from the set of existing attributes the system may determine that the set of existing attributes is missing an attribute required by the document registry. For example, if one or more of the required attribute fields is missing from the set of existing attributes, the analysis server may determine that the document is not XDS compatible.

In a step 720, the system obtains the missing metadata attribute. In a step 725, the system augments the set of existing attributes with the missing metadata attribute. The augmentation may include appending, adding, or inserting the newly obtained metadata attribute to the existing attributes. As discussed above, in some cases a legacy document may not have any existing attributes and the augmentation may include associating the newly obtained attributes with the document.

In a step 730, the system packages and transmits the augmented set of attributes and the document to a document repository. In turn, the document repository forwards the augmented set of attributes to the document registry for storage at the registry. The document is stored at the repository. In another specific implementation, the system transmits the augmented set of attributes to the document registry and the document to the document repository. This can help to reduce the computing resources needed by the document repository because the repository will not have to forward the augmented set of attributes to the document registry.

Figure 8:
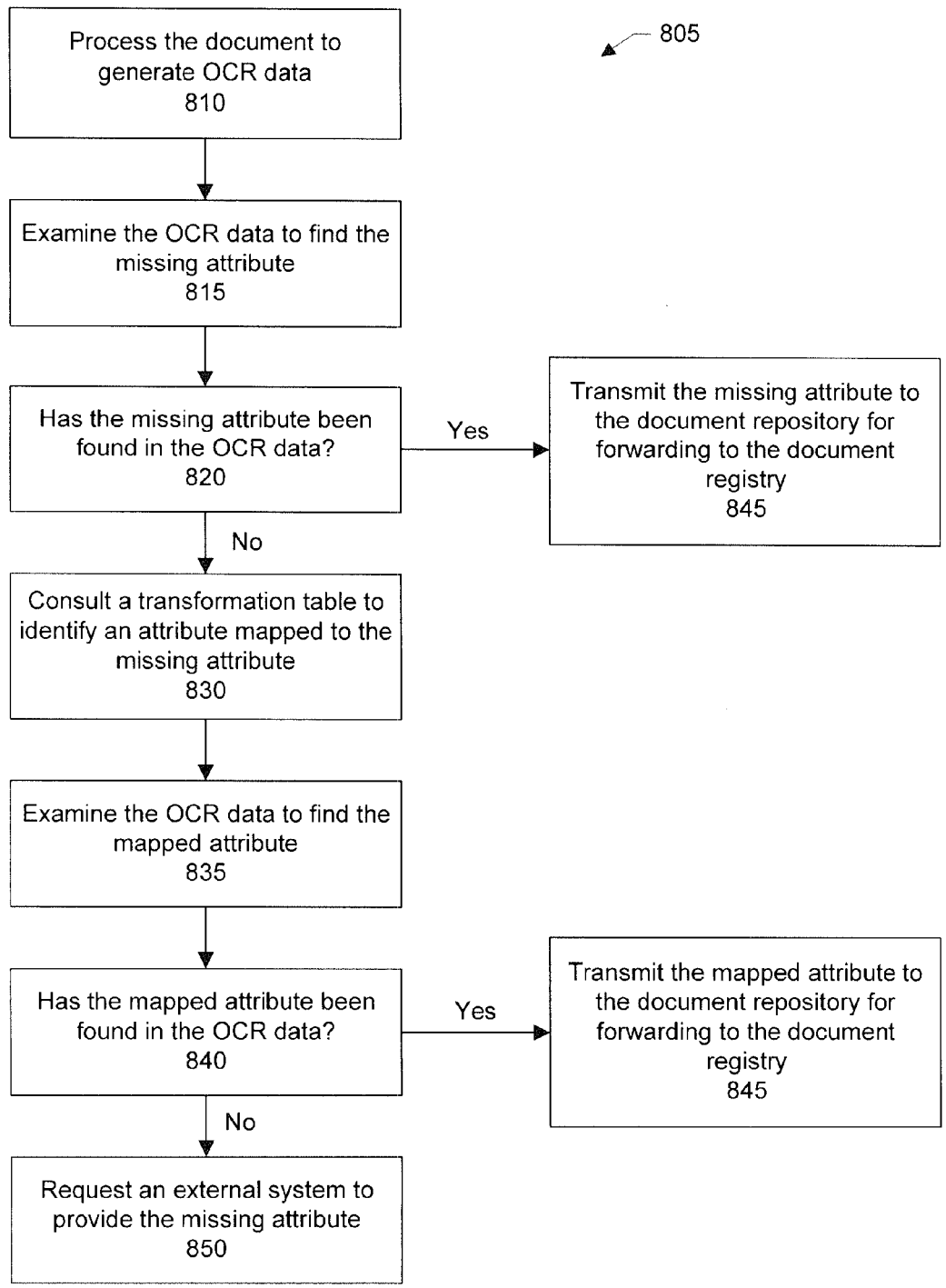
FIG. 8 shows a flow of a specific implementation for obtaining missing attributes.

FIGS. 8-11 and the accompanying descriptions provide further details for obtaining the associated document metadata attribute information that may be required by the document registry. FIG. 8 shows a flow 805 for deriving or inferring the missing metadata attribute required by the document registry from the document content itself. In a step 810, the system processes the document to generate OCR data. In a step 815, the system examines the OCR data to find the missing attribute.

For example, the document registry may require that registry entry include the name of the hospital where the patient services were rendered. A set of existing attributes associated with a legacy document may not include the hospital name. For example, the set of existing attributes may include the patient name, but not the hospital name. The hospital name, however, may be listed in the document. Thus, the hospital name may be found by examining the OCR data. The data miner may use any feature recognition technique or combination of techniques to search the OCR data for the required attribute. Some examples of feature recognition techniques include keyword searching, proximity-based searching, template-based recognition, dictionaries, taxonomies, and others.

The data miner may, for example, search for the keyword "Hospital" in the OCR data. Upon finding the keyword, the data miner may determine that one or more other words following the keyword "Hospital" is the missing attribute value, e.g., "Saint Mary Medical Center." In some cases, the document may have a structured format or layout. For example, the hospital name may be listed in the top right hand corner of the document. In a specific implementation, the system allows a user to designate one or more document zones or areas from which to extract the attribute value. For each of the various document types, the user may define a document template that designates a particular area on a document where the required attribute value may be found. In another specific implementation, the data miner may use the keyword (e.g., "hospital") as an anchor word and find the attribute value (e.g., "Saint Mary Medical Center") by looking for words near the anchor word.

In a step 825, if the missing attribute has been found, the system transmits the missing metadata attribute, document, or both to the document repository. The document repository forwards the attribute to the document registry. The document remains stored at the repository. In the example above, the system may transmit the attribute field value "Saint Mary Medical Center" to the repository. This allows the document to be searched via the repository using the attribute field "Hospital."

In a step 830, if the missing attribute has not been found, the system consults a transformation table to identify an attribute that may be mapped to the missing attribute. In a step 835, the system examines or reexamines the OCR data to find the mapped attribute. FIG. 9 shows an example of a transformation table 905. In this example, the transformation table includes a first list of required attribute fields 910, and a second list of equivalent attribute fields 915. Each required attribute field is mapped to at least one equivalent attribute field. For example, "author" is mapped to "creator," "hospital" is mapped to "institution," and "facility," and "date of service" is mapped to "date of exam," and "date of procedure."

In some cases, the document may not explicitly include the required attribute, but may include an equivalent attribute. For example, the document registry may require that each document stored in the document repository have a registry entry that identifies the hospital associated with the stored document. The transformation table allows users to define one or more attributes (or field names) that are equivalent to the required attribute.

For example, using the transformation table, a user can define the required attribute "hospital" to be equivalent to "institution," or "facility." Thus, if the data miner is unable to find the attribute "hospital" in the OCR data, the data miner may consult the transformation table to determine whether there have been any equivalent attributes mapped to "hospital." In this example, the terms "institution" and "facility" have been mapped to "hospital." Thus, the data miner may search the OCR data for the equivalent attribute fields, i.e., the terms "institution," "facility," or both. Upon finding an equivalent attribute field, the system can extract the corresponding attribute field value, e.g., "Saint Mary Medical Center" and transmit the value to the document repository for the repository to forward to the registry—see steps 840 and 845 (FIG. 8).

Figure 10:
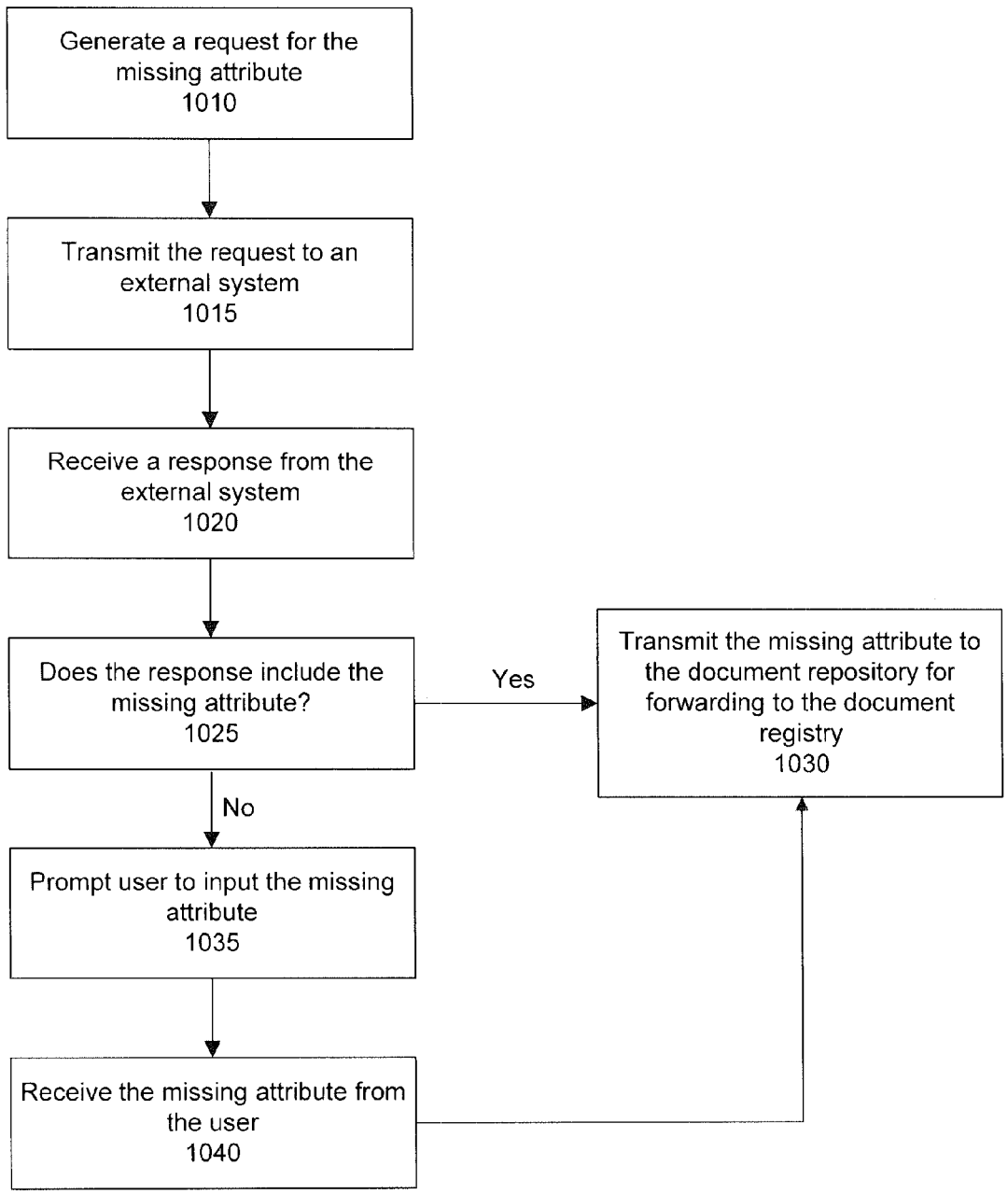
FIG. 10 shows a flow of another specific implementation for obtaining missing attributes.

In a step 850, if the mapped attribute is not found in the OCR data the system may request the attribute from an external system. FIG. 10 shows a flow 1005 for the making the request. In a step 1010, the system generates a request for the missing attribute. In a step 1015, the system transmits the request to an external system.

In a specific implementation, the request is transmitted through a web service. A web service is a method of communication between two electronic devices over the web or Internet. The request may include the attribute for which a value is needed and other context information that may assist the external service in determining the attribute value. For example, the context information may include one or more pieces of information included in the document to be registered such as a patient identifier, patient name, document title, document type, date of service, time of service, primary care physician, medical procedure performed, ordering physician, patient date of birth, billing number, account number, or combinations of these.

In a step 1020, the system receives a response from the external system. If the response includes the missing attribute value, the system transmits the value to the document repository for the repository to forward to the document registry (steps 1025 and 1030). In a step 1035, if the response from the external system does not include the missing attribute value, the system may prompt the user to input the value. For example, the system may display an input box on a graphical user interface for the user to supply the missing attribute value. The user may use a keyboard or other input device to enter the value.

In a step 1040, the system receives the missing attribute from the user and transmits the attribute to the document repository for the repository to forward to the document registry (step 1030).

Figure 11:
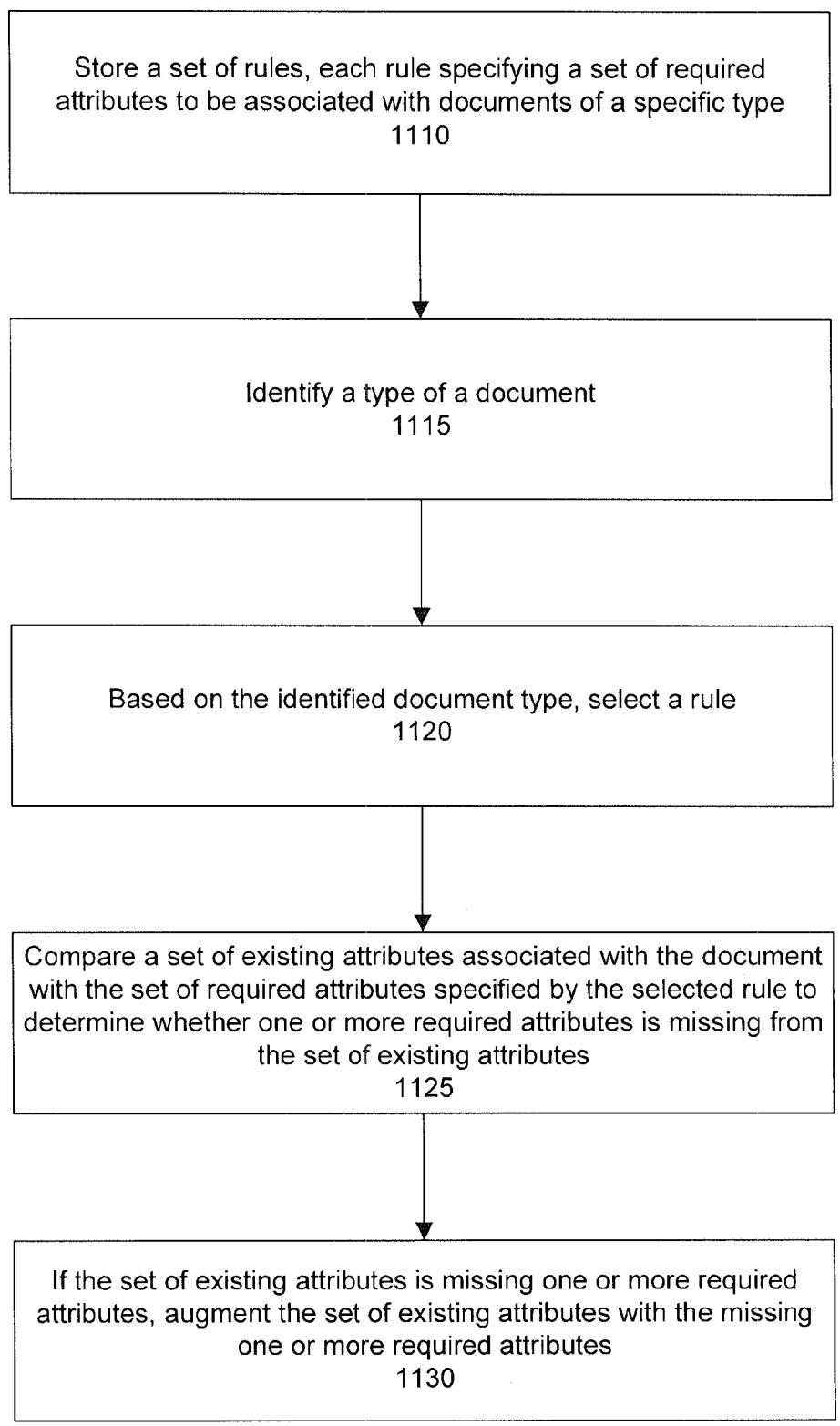
FIG. 11 shows a flow of another specific implementation for obtaining missing attributes.

FIG. 11 shows an overall flow 1105 for using a rule to augment an existing set of attributes associated with legacy document. In a step 1110, the system stores a set of rules. Each rule specifies a set of attributes, required by a document registry, to be associated with documents of a specific type.

In a step 1115, the system identifies a type of a document. In a specific implementation, document types are identified by analyzing the document content, attributes, or both. Examples of analysis techniques include data mining, pattern recognition, keyword searching, and others.

In a step 1120, based on the identified document type, a rule is selected. A rule can be specific to a particular document type. There can be a rule that applies to patient consent forms, a rule that applies to discharge instructions, a rule that applies to lab results, and so forth.

In a step 1125, the system compares a set of existing attributes associated with the document with a set of required attributes specified by the selected rule to determine whether one or more required attributes is missing from the set of existing attributes. If the set of existing attributes is missing one or more required attributes, the system augments the set of existing attributes with the missing one or more required attributes.

For example, the document type may be identified as a patient consent form. A rule for patient consent forms may specify that patient consent forms should include the attribute "date signed." If the set of existing attributes associated with the legacy document, e.g., a scanned patient consent form, does not include the attribute "date signed" the system augments the set of existing attributes with the "date signed" attribute. The value for the attribute may be obtained by mining the document content (see FIG. 8 and accompanying discussion), requesting the value from an external system, or prompting a user (see FIG. 10 and accompanying discussion).

In a specific implementation, the system allows the user (e.g., healthcare provider or hospital) to configure or identify the required attributes for storing the document in the document repository and registering the document in the document registry. This allows the user to customize the system to fit their needs. In a specific implementation, formatting a set of existing attributes associated with a legacy document may include removing one or more attributes if the one or more attributes are not permitted by the document registry.

This patent application describes systems and techniques for ensuring legacy patient clinical documents are XDS compliant so that the documents can be introduced into an XDS system. Aspects of the invention, however, may be used to ensure that such legacy documents or, alternatively, other non-healthcare related documents are compatible with other standards.

In the description above and throughout, numerous specific details are set forth in order to provide a thorough understanding of an embodiment of this disclosure. It will be evident, however, to one of ordinary skill in the art, that an embodiment may be practiced without these specific details. In other instances, well-known structures and devices are shown in block diagram form to facilitate explanation. The description of the preferred embodiments is not intended to limit the scope of the claims appended hereto. Further, in the methods disclosed herein, various steps are disclosed illustrating some of the functions of an embodiment. These steps are merely examples, and are not meant to be limiting in any way. Other steps and functions may be contemplated without departing from this disclosure or the scope of an embodiment.

What is claimed is:

1. A computer-implemented method comprising:
reviewing, by a computer system having a processor, a set of existing attributes associated with a document;
determining, by the computer system, that the set of existing attributes is missing at least one attribute that is required by a document registry by comparing the set of existing attributes associated with a document with a set of attributes required the document registry;
obtaining, by the computer system, the missing at least one attribute by at least one of mining contents of the document, requesting a value from an external system, and prompting a user input;
augmenting, by the computer system, the set of existing attributes with the missing at least one attribute; and
transmitting, by the computer system, the augmented set of existing attributes and the document to a document repository, wherein the document repository forwards the augmented set of existing attributes to the document registry for storage of the augmented set of existing attributes at the document registry, and the document is stored separate from the augmented set of existing attributes at the document repository.

2. The method of claim 1 further comprising:
processing the document with an optical character recognition engine to generate optical character recognition data,
wherein examining the data relating to the document to search for the first field name comprises examining the optical character recognition data to find the field name, and
wherein identifying the field value corresponding to the second field name in the data relating comprises identifying the field value in the optical character recognition data.

3. The method of claim 1 further comprising:
transmitting, through a web service, a request to an external system for the missing at least one attribute when the first field name is not found in the transformation table;
receiving the missing at least one attribute from the external system; and transmitting the missing at least one attribute to the document repository for the document repository to forward to the document registry.

4. The method of claim 3 further comprising:
prompting the user to input a field value for the first field name when the first field name is not found in the transformation table;
receiving the field value; and
transmitting the field value for the missing at least one attribute to the document repository for the document repository to forward to the document registry.

5. The method of claim 1 comprising:
storing a plurality of rules, each rule specifying a set of attributes required by the document registry;
identifying a type of the document;
based on the identified document type, selecting a rule, wherein the attributes required by the document registry is specified by the selected rule to determine whether one or more required attributes is missing from the set of existing attributes; and
determining that a required attribute is missing from the set of existing attributes, the required attribute being the missing at least one attribute.

6. The method of claim 1 wherein the first field is mapped to the second field in the transformation table.

7. The method of claim 6 wherein the mapping of the first field to the second field indicates that the first field and the second field have equivalent attributes.

8. A computer program product, comprising a computer-readable program code to be executed by one or more processors when retrieved from a non-transitory computer readable medium, the computer-readable program code including instructions to:
review a set of existing attributes associated with a document;
determine that the set of existing attributes is missing at least one attribute that is required by a document registry, by comparing the set of existing attributes associated with a document with a set of attributes required by the document registry, wherein the missing at least one attribute comprises a first field name;
examine data relating to the document to search for the first field name;
consult a transformation table comprising the first field name and a second field name when the first field name is not found in the data, the second field name identified by the transformation table as being equivalent to the first field name;
identify a field value corresponding to the second field name in the data relating to the document, and
transmit the document and the field value for the missing at least one attribute to a document repository for forwarding to the document registry to augment the set of existing attributes, wherein the document is stored separate from the augmented set of existing attributes at the document repository.

9. The computer program product of claim 8 further comprising instructions to:
process the document with an optical character recognition engine to generate optical character recognition data,
wherein the instructions to examine the data relating to the document to find the first field name comprises instructions to examine the optical character recognition data to find the field name, and
wherein instructions to identify the field value corresponding to the second field name in the data comprises instructions to identify the field value in the optical character recognition data.

10. The computer program product of claim 8 further comprising instructions to:
transmit, through a web service, a request to an external system for the missing at least one attribute when the first field name is not found in the transformation table;
receive the missing at least one attribute from the external system; and
transmit the missing at least one attribute to the document repository for the document repository to forward to the document registry.

11. The computer program product of claim 10 further comprising instructions to:
when the first field name is not found in the transformation table, prompt the user to input a field value for the first field name;
receive the field value; and
transmit the field value for the missing at least one attribute to the document repository for the document repository to forward to the document registry.

12. The computer program product of claim 8 further includes instructions to:
store a plurality of rules, each rule specifying a set of attributes required by the document registry;
identify a type of the document;
based on the identified document type, select a rule,
wherein the attributes required by the document registry is specified by the selected rule to determine whether one or more required attributes is missing from the set of existing attributes; and
determine that a required attribute is missing from the set of existing attributes, the required attribute being the missing at least one attribute.

13. The computer program product of claim 8 wherein the first field is mapped to the second field in the transformation table.

14. The computer program product of claim 13 wherein the mapping of the first field to the second field indicates that the first field and the second field have equivalent attributes.

15. A system for permitting a document to be registered in a document registry that complies with a cross-enterprise document sharing ("XDS") standard, the system comprising:
a processor-based database management application, which when executed on a computer system, will cause the processor to:
review a set of existing attributes associated with a document;
determine that the set of existing attributes is missing at least one attribute that is required by a document registry, by comparing the set of existing attributes associated with a document with a set of attributes required by the document registry, wherein the missing at least one attribute comprises a first field name;
examine data relating to the document to search for the first field name;
consult a transformation table comprising the first field name and a second field name when the first field name is not found in the data, the second field name identified by the transformation table as being equivalent to the first field name;
identify a field value corresponding to the second field name in the data relating to the document, and
transmit the document and the field value for the missing at least one attribute to a document repository for forwarding to the document registry to augment the set of existing attributes, wherein the document is stored separate from the augmented set of existing attributes at the document repository.

16. The system of claim 15 will further causes the processor to:
    process the document with an optical character recognition engine to generate optical character recognition data,
    wherein the instructions to examine the data relating to the document to find the first field name comprises instructions to examine the optical character recognition data to find the field name, and
    wherein instructions to identify the field value corresponding to the second field name in the data comprises instructions to identify the field value in the optical character recognition data.

17. The system of claim 15 will further cause the processor to:
    transmit, through a web service, a request to an external system for the missing at least one attribute when the first field name is not found in the transformation table;
    receive the missing at least one attribute from the external system; and
    transmit the missing at least one attribute to the document repository for the document repository to forward to the document registry.

18. The system of claim 17 will further cause the processor to:
    prompt the user to input a field value for the first field name when the first field name is not found in the transformation table;
    receiving receive the field value; and
    transmitting transmit the field value for the missing at least one attribute to the document repository for the document repository to forward to the document registry.

19. The system of claim 15 wherein the processor-based database management application will further cause the processor to:
    store a plurality of rules, each rule specifying a set of attributes required by the document registry;
    identify a type of the document;
    based on the identified document type, select a rule,
    wherein the attributes required by the document registry is specified by the selected rule to determine whether one or more required attributes is missing from the set of existing attributes; and
    determine that a required attribute is missing from the set of existing attributes, the required attribute being the missing at least one attribute.

20. The system of claim 15 wherein the first field is mapped to the second field in the transformation table, and wherein the mapping of the first field to the second field indicates that the first field and the second field have equivalent attributes.

* * * * *